United States Patent [19]

Weber et al.

[11] Patent Number: 5,753,647
[45] Date of Patent: May 19, 1998

[54] ACYLAMINO-SUBSTITUTED HETRAZEPINES

[75] Inventors: Karl-Heinz Weber, Gau-Algesheim; Werner Stransky, GauAlgesheim; Ulrike Küfner-Mühl, Ingelheim am Rhein; Hubert Heuer, Ingelheim am Rhein; Franz Birke, Ingelheim Rhein, all of Germany

[73] Assignee: Boehringer Ingelheim KG, Ingelheim am Rhein, Germany

[21] Appl. No.: 350,196

[22] Filed: Dec. 5, 1994

Related U.S. Application Data

[63] Continuation of Ser. No. 152,045, Nov. 12, 1993, abandoned, which is a continuation of Ser. No. 848,575, Mar. 9, 1992, abandoned.

[30] Foreign Application Priority Data

Mar. 8, 1991 [DE] Germany ............ 41 075 21.8

[51] Int. Cl.⁶ .................. C07D 495/22; A61K 31/55
[52] U.S. Cl. ............................. 514/219; 540/555
[58] Field of Search ....................... 540/555; 514/219

[56] References Cited

U.S. PATENT DOCUMENTS 5,304,553  4/1994  Okano et al. .................. 514/219

FOREIGN PATENT DOCUMENTS

| 0230942 | 8/1987 | European Pat. Off. . |
|---|---|---|
| 254245 | 1/1988 | European Pat. Off. . |
| 0328924 | 8/1989 | European Pat. Off. . |
| 0368175 | 5/1990 | European Pat. Off. . |
| 367110 | 5/1990 | European Pat. Off. . |

OTHER PUBLICATIONS

Miyazawa et al, Chem. Pharm. Bull 39(12), pp. 3215–3220 (1991).

*Primary Examiner*—John M. Ford
*Attorney, Agent, or Firm*—R. P. Raymond; M-E. M. Devlin; A. R. Stempel

[57] ABSTRACT

A hetrazepine of the formula given below and a pharmaceutical composition comprising a therapeutically effective amount of the hetrazepine and a pharmaceutically acceptable inert carrier are disclosed and are useful in treating disease in a warm-blooded animal induced by endogenously formed PAF;

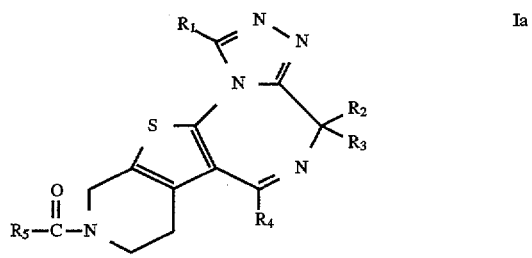

wherein the substituents are defined herein.

10 Claims, No Drawings

ACYLAMINO-SUBSTITUTED HETRAZEPINES

This is a continuation of application Ser. No. 08/152,045, filed Nov. 12, 1993, now abandoned, which is a continuation of application Ser. No. 07/848,575, filed Mar. 9, 1992, now abandoned.

The invention relates to new acylamino-substituted hetrazepines, processes for their preparation and their use as pharmaceutical compositions.

Hetrazepines with a PAF-antagonistic effect are known from various European patent applications, e.g., from European Patent Applications 254 245, 328 924 and 407 955. Surprisingly, it has been found that hetrazepines which contain an acylamino group as a structural element have better pharmacological properties.

The new hetrazepines correspond to general formula I, wherein $R_1$ represents hydrogen, halogen, a branched or unbranched $C_{1-4}$-alkyl group, preferably methyl, which may optionally be substituted by hydroxy or halogen, or a cyclopropyl or cyclobutyl group;

$R_2$ represents hydrogen, methyl, trifluoromethyl or hydroxymethyl;

$R_3$ represents hydrogen, methyl, trifluoromethyl or hydroxymethyl;

$R_4$ represents phenyl, whilst the phenyl ring may be mono- or polysubstituted, preferably in the 2-position, by methyl, preferably by halogen and more especially by chlorine or bromine, nitro, alkoxy, preferably methoxy and/or trifluoromethyl, or $R_4$ may represent pyridyl or thienyl which may optionally be substituted by $C_{1-4}$-alkyl or halogen;

X represents nitrogen or C—H;

A represents a group of formula a)

wherein n=1, 2 or 3 m=1, 2 or 3 and m+n=2, 3 or 4;

b)

or c)

wherein B=$CH_2$ or —$CH_2$—$CH_2$—
wherein $R_5$ represents an optionally substituted $C_{1-8}$-alkyl, preferably $C_{1-4}$-alkyl group, an optionally substituted aryl group, $CH_2$-aryl or $CH_2$—$CH_2$-aryl;

$R_6$ represents hydrogen or an optionally substituted $C_{1-8}$-alkyl, preferably $C_{1-4}$-alkyl group; an optionally substituted benzyl group and Z represents a $C_{1-8}$-alkyl group;

$Z_n$ represents a $C_{1-8}$-alkyl group or a single bond, optionally in the form of the racemates, enantiomers, diastereomers and mixtures thereof.

The preferred compounds are hetrazepines of general formula I

-continued

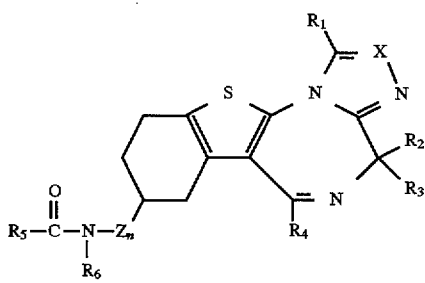

wherein $R_1$ represents $CH_3$;

$R_2$ represents hydrogen or methyl;

$R_3$ represents hydrogen or methyl;

$R_4$ represents ortho-chlorophenyl;

$R_5$ represents $C_{1-4}$-alkyl, optionally substituted phenyl, optionally substituted —$CH_2$—phenyl, optionally substituted thiophene, optionally substituted furan, optionally substituted pyridine;

$R_6$ represents hydrogen or $C_{1-4}$-alkyl;

Z represents a linear $C_{1-4}$-alkyl group, preferably $CH_2$;

$Z_n$ represents a linear $C_{1-4}$-alkyl group or a single bond; optionally in the form of the racemates, enantiomers, diastereomers and mixtures thereof.

Particularly preferred compounds are those of general formula

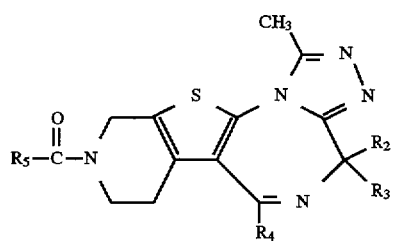

wherein $R_2$ represents hydrogen or methyl;

$R_3$ represents hydrogen;

$R_4$ represents ortho-chlorophenyl;

$R_5$ represents a group

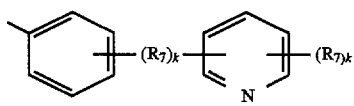

wherein $R_7$ represents hydrogen, halogen, hydroxy, nitro, cyano, trifluoromethyl, branched or unbranched $C_{1-8}$-alkyl, preferably $C_{1-4}$-alkyl, optionally substituted by halogen or hydroxy, optionally substituted $C_{3-6}$-cycloalkyl, optionally substituted by halogen or hydroxy, optionally substituted branched or unbranched $C_{1-8}$-alkoxy, preferably $C_{1-4}$-alkoxy, $C_{1-4}$-alkyl-S-, HS-, amino, $C_{1-6}$-alkylamino, $C_{1-6}$-dialkylamino, k=1, 2 or 3, whilst if k is greater than 1 $R_4$ may be identical or different;

$R_5$ represents a group

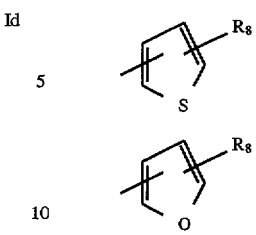

wherein $R_8$ may represent hydrogen, halogen or $C_{1-4}$-alkyl, optionally in the form of their racemates, enantiomers, diastereomers and mixtures thereof.

Preferred groups $R_5$ of general formula Ia are groups of general formula

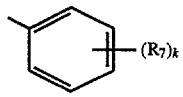

wherein $R_7$ represents hydrogen, halogen, methyl, ethyl, iso-butyl, tert.-butyl or methoxy, whilst it is particularly preferred for the group $R_7$ to be in the 4-position of the phenyl ring.

The compounds according to the invention may have a center of asymmetry in the diazepine ring if $R_2$ and $R_3$ are differently substituted.

The mixtures of optically isomeric compounds which may be obtained during the synthesis can be separated into the individual optical isomers by the formation of diastereomers and by the following methods known per se, e.g., crystallization or chromatographic or enzymatic separation processes. Thus, for example, they may be separated by liquid chromatography using cellulose triacetate as the stationary phase. Unless otherwise stated specifically, the general definitions are used in the following sense:

Alkyl in general represents an unbranched or branched hydrocarbon radical having 1 to 8 carbon atom(s), which can optionally be substituted by one halogen atom or several halogen atoms—preferably fluorine—which can be identical to one another or different, lower alkyl radicals being preferred for a branched or unbranched hydrocarbon radical having 1 to about 4 carbon atom(s). Halogen denotes fluorine, chlorine, bromine and iodine.

Preferred alkyl groups (also where these are constituents of other radicals) are, unless stated otherwise, methyl, ethyl, propyl, iso-propyl, n-propyl, n-butyl, iso-butyl, sec.-butyl and tert.-butyl.

According to the invention, the alkylene groups Z and $Z_n$ which connect the acylamino group ($R_5CONR_6$—) are also termed alkyl groups in order to avoid any misinterpretation of the term "alkylene". Cycloalkyl generally represents a saturated or unsaturated cyclic hydrocarbon group having 3 to 6 carbon atoms which may optionally be substituted by a halogen atom or several halogen atoms of a hydroxy group, an alkyl group, preferably methyl, which may be identical or different from one another. Examples include cyclopropyl, cyclobutyl, cyclopentyl, cyclopentenyl, cyclohexyl, cyclohexenyl.

Phenyl groups may, for example, be substituted by one or more lower alkyl groups, alkoxy groups, nitro groups, amino groups and/or one or more halogen atoms, which may be identical to or different from one another. Unless otherwise stated, the term aryl means optionally mono- or polysubstituted aromatic groups having up to 10 carbon atoms in the ring system, such as phenyl, pyridyl, thienyl, furyl or naphthyl, the phenyl ring being preferred. Unless specifically otherwise stated, the substituents may be one or more atoms selected from the group comprising halogen, one or more groups selected from alkyl, alkoxy, amino, alkylamino and dialkylamino and hydroxy, whilst methyl, isobutyl, hydroxy and trifluoromethyl are preferred.

A substituted phenyl group may, for example, also carry one or more of the substituents mentioned below: $C_{1-6}$-alkyl, $C_{1-6}$-alkoxy, halogen, amino, alkylamino, dialkylamino, $CF_3$, $C_{3-6}$-cycloalkyl, cyano, $NO_2$, COH, COOH, $COOC_{1-4}$-alkyl, cyclopropyl, hydroxy, SH, S—$C_{1-4}$-alkyl, hydroxymethyl.

Examples of substituted phenyl are as follows:

3-chlorophenyl, 4-chlorophenyl, 3-bromophenyl, 4-bromophenyl, 4-fluoromethyl, 2-chlorophenyl, 2-bromo-phenyl, 3-fluorophenyl, 2,3-dichlorophenyl, 2-methylphenyl, 4-methylphenyl, 3-ethylphenyl, 4-propylphenyl, 4-isopropylphenyl, 4-butylphenyl, 4-tert-butylphenyl, 4-iso-butylphenyl, 4-pentylphenyl, 2,4-dimethylphenyl, 2-trifluoromethylphenyl, 3-trifluoro-methylphenyl, 4-trifluoromethylphenyl, 2-methoxyphenyl, 4-methoxyphenyl, 3-ethoxyphenyl, 2-propoxyphenyl, 4-butoxyphenyl, 2,4-dimethoxyphenyl, 3,4,5-trimethoxyphenyl, 2,3,4,5,6-pentafluorophenyl.

Alkoxy generally represents a straight-chained or branched $C_{1-8}$-hydrocarbon group bound via an oxygen atom. An alkoxy group having 1 to 4 carbon atoms is particularly preferred. Examples include methoxy, ethoxy, propoxy, isopropoxy, butoxy, isobutoxy, tert.-butoxy, pentoxy, isopentoxy, hexoxy, isohexoxy, heptoxy, isoheptoxy, octoxy or isooctoxy.

In pharmacological experiments, PAF shows bronchioconstriction, a reduction in blood pressure, inducement of platelet aggregation and a proinflammatory action.

These experimentally detectable actions of PAF directly or indirectly indicate possible functions of this mediator in anaphylaxis, in the pathophysiology of bronchial asthma and generally in inflammation.

PAF antagonists are required on the one hand to clarify further pathophysiological functions of this mediator in animals and humans and on the other hand to treat pathological conditions and diseases in which PAF participates. Examples of the indications of a PAF antagonist are inflammation processes of the tracheobronchial tree (acute and chronic bronchitis, bronchial asthma) or of the kidney (glomerulonephritis), of the joints (rheumatic diseases), anaphylactic states, allergies and inflammations in the region of the mucosa (e.g. allergic rhinitis) and skin (e.g. psoriasis) and shock states caused by sepsis, endotoxins or burns. Other important indications for a PAF antagonist are lesions and inflammations in the region of the gastric and intestinal mucosa, such as e.g. gastritis, peptic ulcers in general, but in particular gastric ulcers and duodenal ulcers; and for treating thrombosis.

The compounds according to the invention are furthermore suitable for the treatment of the following diagnoses: Obstructive pulmonary diseases, bronchial hyperreactivity, inflammatory diseases of the pulmonary tract, such as e.g. chronic bronchitis; fibrotic diseases of the pulmonary tract such as fibrosing alveolitis and interstitial pneumonitis syndrome; gynaecological diseases e.g. dysmenorrhea, eclampsia in pregnancy, high blood pressure in pregnancy; inhibition of labor; cardiovascular diseases, such as e.g. polytrauma, anaphylaxis, arteriosclerosis; diseases of defective vascular formation, e.g. defective vascular formation in the eyes; EPH gestosis (oedema- proteinuria-hypertension); inflammatory and immunological diseases, immunomodulation for transplants of foreign tissues, immunomodulation for leukaemia, the spread of metastases, e.g. with bronchial neoplasia; the compounds according to the invention furthermore prove to be cyto- and organoprotective, e.g. for neuroprotection, e.g. in cases of cirrhosis of the liver, e.g. protection in radiotherapy, e.g. for use during or after surgical intervention and in extracorporal circulation; DIC (disseminated intravasal coagulation); for use in organ transplantation, for reducing side effects of drug therapy, e.g. anaphylactoid circulatory reactions, contrast medium incidents, side effects of tumor therapy, hemolytic uremic syndrome; hepta-renal syndrome, incompatibilities in blood transfusions; liver failure (e.g. hepatitis, primary biliary cirrhosis, primary sclerosing cholangitis), poisoning, e.g. Amanita phalloides intoxication (death-head intoxication); symptoms of parasitic diseases (e.g. worm diseases); autoimmune diseases.

The following indications are also of interest:

Immune function in cases of Aids, diabetes, juvenile diabetes, diabetic retinopathy, polytraumatic shock, haemorrhagic shock, NS disorders such as migraine, agarophobia (panic disorder): ischaemia, multiple sclerosis; inflammatory intestinal diseases; ulcerative colitis, Crohn's disease: pulmonary hypertension and chronic ischaemic cardiac insufficiency, PAF-antagonists of general formula I are suitable for treating pathological changes in the blood gases such as respiratory acidosis and metabolic alkalosis. On their own or in conjunction with anticholinergics, PAF-antagonists can be used to improve the blood gas values in cases of phosphoric acid ester poisoning. It is known that PAF-antagonists alone—or in conjunction with immunosuppressant compounds (e.g. cyclosporins or FK-506)—can be used to treat asthma, autoimmune diseases and in transplants, achieving not only an improved effects but also a reduction in the toxicity of cyclosporins or FK-506.

It is also proposed to use PAF-antagonists in conjunction with antihistamines. For the definition of antihistamines, reference is made to European Patent Application 345 731. It is also known that PAF-antagonists can be used in conjunction with $\beta_2$-mimetics for treating bronchial asthma PAF-associated interaction with tissue hormone (autocoid hormones), lymphokines and other mediators is known. PAF-antagonists are also suitable for treating the diseases caused by reduced $\beta$-receptor stimulation in the heart or diseases caused by Down Regulation of the,$\beta$-receptors in the heart, e.g. for treating the inadequate pumping action of the heart in cases of acute heart failure, e.g. after myocardial infarct and cardiogenic shock, or in chronic cardiovascular diseases such as congestive heart insufficiency, heart insufficiency after myocardial infarct or in cases of ischaemic cardiomyopathy.

They may also be used in combination, particularly for those indications for which PAF-antagonists are suitable. Accordingly, the PAF-antagonists may be combined, for example, with $\beta$-adrenergics, parasympatholytics, corticosteroids, antiallergic agents, secretolytics and antibiotics. When they are combined with TNF (tumor necrosis factor) improved tolerance of the TNF is achieved (elimination of undesirable side effects); TNF can therefore be used in higher doses, if desired, than when it is used on its own.

(The term "combination" here includes the use of the two active substances in separate preparations and at a certain time interval). When the compounds according to the invention are administered jointly with β-adrenergics, a synergistic effect can be achieved, e.g. in broncholysis. It is also very beneficial to combine the PAF-antagonists with immunosuppressants, e.g. the various cyclosporins.

Aqueous solutions containing one of the compounds according to the invention are suitable for the storage of organs intended for transplantation. PAF-antagonists are suitable as an additive to preserved blood and plasma.

The new compounds may be administered by topical, oral or parenteral route or by inhaling. The compounds are present as active ingredients in conventional preparations, e.g. in compositions consisting essentially of an inert pharmaceutical carrier and an effective dose of the active substance, e.g. plain or coated tablets, capsules, lozenges, powders, solutions, suspensions, aerosols for inhalation, ointments, emulsions, syrups and suppositories.

The therapeutic and prophylactic dose depends on the nature and gravity of the disease. An effective dose of the compounds according to the invention, for oral administration, is between 1 and 200, preferably between 10 and 80 mg/dose and for intravenous or intramuscular administration between 0.001 and 50, preferably between 0.1 and 30 mg/dose. For inhalation, solutions containing 0.01 to 1.0, preferably 0.1 to 0.5% of active substance should be used, as well as powders and suspensions in liquefied propellant gases.

The new hetrazepines are very potent PAF antagonists and are superior to other known diazepinoid PAF antagonists in the following criteria:
  there is total dissociation between the PAF antagonism and the effects mediated to the benzodiazepine receptor;
  superior binding affinity with the PAF receptor on washed human platelets, and they exhibit a greater inhibition of PAF-induced platelet aggregation;
  they moreover inhibit, in a superior manner, bronchioconstriction induced by PAF (30 ng/kg×min) after oral and parenteral administration to guinea pigs, in combination with a very long action time (more than 15 h after oral administration to guinea pigs).

The inhibition of PAF-induced platelet aggregation can be determined by the following method.

200 ml samples of blood were taken from a non-obstructed vein, with the aid of a plastic syringe containing 3.8% sodium citrate solution, from healthy male and female donors aged from 18 to 35 years who had not taken any medicaments (aspirin or other non-steroid anti-inflammatories) for several days before the blood withdrawal. The ratio of sodium citrate solution:blood was 1:9. The citrated blood was centrifuged in plastic tubes at 150×g (=1,200 rpm) at room temperature for 20 min (Heraeus Christ bench centrifuge 124).

The platelet aggregation was measured in vitro by the method of Born and Cross (1963), an aggregation inducer (PAF) being added to the TRP, while stirring constantly. For the measurement, 0.8 ml TRP and 0.2 ml modified Tyrode's solution (see below) were introduced into 1 ml plastic cells, each of which contained a small metal pin (stirrer, 1,000 rpm). The test substance was added in a volume of 10 μl 2 to 3 min before inducing the aggregation. Either DMSO and water or a dilute HCl solution was used as the solvent. The control batches contained the corresponding volume of these solvents. After recording the initial absorption (2–3 min), aggregation was induced. PAF ($5 \times 10^{-8}$ M; Bachem Feinchemikalien) was introduced into the cell in a volume of 10 μl.

The modified Tyrode's solution had the following composition: 136.9 mM NaCl; 2.68 mM KCl; 0.5 mM $MgCl_2$; 1.8 mM $CaCl_2$; 0.42 mM $NaH_2PO_4$; 5.55 mM glucose and 11.9 mM $NaHCO_3$.

To evaluate substance effects, the maximum of the first aggregation wave was used. The maximum absorption induced by the aggregation inducer (=maximum aggregation=100%) was simultaneously run in a parallel batch (in the 2nd channel of the aggregometer) to each test batch and used as the 100% value. The aggregation value achieved under the action of the test substance was quoted as % of the control value (batch). Concentration/effect curves with a random sample size of in each case n=4 were plotted with the aid of this method and $IC_{50}$ values (concentration at 50% aggregation inhibition) were calculated.

[$^3$H]PAF-Receptor-Bonding to Vital Human Blood Platelets

The competitive interaction of test substances (here PAF-antagonists) with the known interaction of the radioligand [$^3$H]PAF to the same receptor is determined. The binding studies are carried out on vital human thrombocytes. Blood samples from healthy donors were diluted with ACD-buffer and centrifuged (15 min., 160×g). The platelet-rich plasma is purified by chromatography on Sepharose CL-2B [using HEPES-buffer, pH 7.4 at 20° C. for eluting].

Defined quantities [e.g. 800 μl] of the platelet suspension were incubated for 90 minutes at ambient temperature, i.e. mixed with:

a) a 30 picomolar [$^3$H]PAF-solution diluted with buffer.

b) a 30 picomolar [$_3$H] PAF-solution which simultaneously contains a μ-molar (unlabelled) PAF-solution, c) with the 30 picomolar [$^3$H]PAF-solution and the solutions of the test substances (different concentrations)

d) used to determine total binding, e) used to determine non-specific binding.

The reaction was stopped by vacuum filtration. The filters with the blood platelets were mixed with scintillation liquid and the residual radioactivity measured in a counter.

The specific binding is obtained from the total binding minus the nonspecific binding. Either the $IC_{50}$ values (i.e. the concentration of test substance which displaces 50% of the radioligand—in this case [$^3$H] PAF—from the receptor) is determined and this is specified, or the $K_i$-values are calculated from this. This may be done by computer-aided calculation using an iteration process of the binding curves. $IC_{50}$ and Ki-values are a measurement of the receptor affinity of the test substance. Lower values indicate a higher affinity.

| Example | [$^3$H]PAF-binding Ki[nM] |
| --- | --- |
| 1 | 2.9 |
| 1a ((−) isomer) | 1.9 |
| 1b ((+) isomer) | 71.0 |
| 2 | 1.8 |
| 20 | 22 |
| 25 | 2.4 |
| 82 | 2.5 |
| 67 | 2.8 |
| 29 | 7.8 |
| 73 | 10.0 |

Compared with 3-cyclopropylcarbonyl-6-(2-chlorophenyl)-11-methyl-2,3,4,5-tetrahydro-4H-pyrido-[4,3:4',5']thieno[3,2-f][1,2,4]triazolo[4,3-a]-1,4-diazepine, having a binding value of Ki=13 [nMol], as known from the prior art (EP 367 110), the compounds claimed according to the invention are significantly superior.

The compounds according to the invention may be prepared by methods analogous to those of the prior art.

The hetrazepines of general formula I according to the invention may be prepared by methods known per se.

Method of synthesis A

Compounds of general formula Ia having a nitrogen-containing heterocyclic group fused onto them, may be obtained, for example, by reacting the correspondingly substituted acid halides—especially acid chlorides—of general formula II

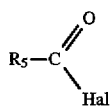

with compounds of general formula III

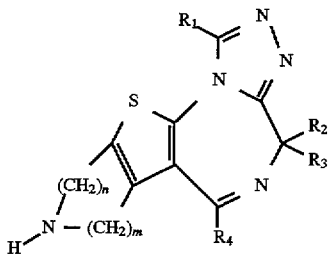

Analogous reactions are described, for example, in European Patent Application 367 110, the contents of which are now referred to.

The reactants may, for example, be reacted in inert organic solvents such as dichloromethane, chloroform, in dialkylethers, e.g. diethylether, tert.-butyl-methylether, tetrahydrofuran, acetone, methylethyl-ketone, benzene, toluene or dimethylformamide, preferably in the presence of an organic or inorganic base such as triethylamine, pyridine, sodium hydrogen carbonate, potassium carbonate or sodium carbonate. If the free acid or a suitable acid anhydride is used instead of the acid chloride of formula II the reaction is preferably carried out in the presence of 1,1-carbonyl-diimidazole, dicyclohexylcarbodiimide or another condensation reagent.

Alternatively, the compounds of general formula Ia may be prepared according to the following synthetic scheme. ($R_4$ preferably represents ortho-chlorophenyl and $R_5$ preferably represents methyl).

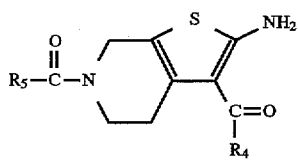

(first step) | $R_2R_3CBr—COBr$      V

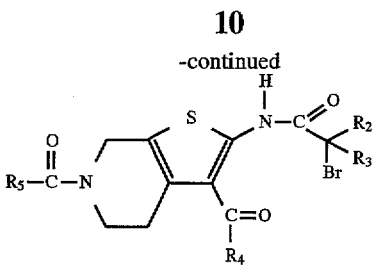

(second step)

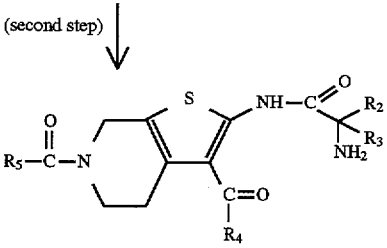

(third step)

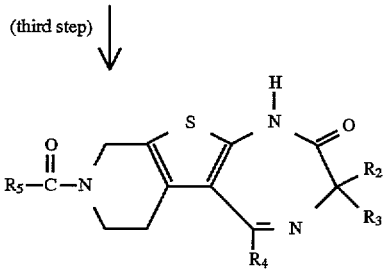

(fourth step) | $P_2S_5$

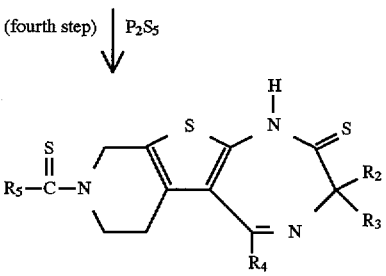

(fifth step)

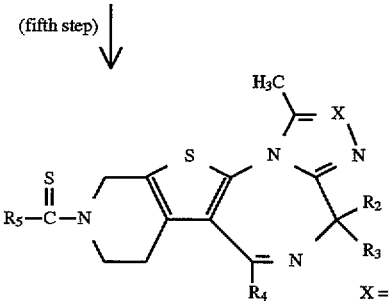

X = N/CH (sixth step)

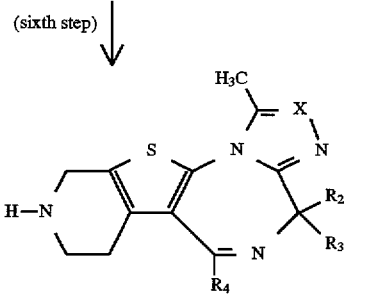

1st Step:

Aminothiophenes of general formula IV are subjected to a condensation reaction with compounds of general formula V under conditions known per se, resulting in compounds of type VI.

For example, a two-phase reaction of an organic solvent, e.g. toluene, benzene, xylene in the presence of a base such as an alkali metal hydroxide, such as sodium hydroxide, potassium hydroxide or in the presence of sodium hydrogen carbonate or potassium hydrogen carbonate. The reaction may also be carried out in the presence of an inert solvent such as dichloromethane, dichloroethane, tetrahydrofuran, toluene, benzene, xylene or dimethylformamide in the presence of a base selected from the group sodium hydroxide, potassium hydroxide, or an alkali metal hydride such as sodium hydride or potassium hydride.

If $R_2$ and $R_3$=hydrogen, the reaction in this step is preferably carried out with chloroacetic acid chloride and if $R_2$=methyl and $R_3$=hydrogen the preferred reagent V is 2-bromopropionic acid bromide, whilst if $R_2$ and $R_3$=methyl the reaction is carried out with 2-bromo-2-methylpropionic acid bromide.

2nd Step

In this step amination is carried out using gaseous ammonia. The reaction takes place at a temperature between 30° and 100° C., either by directly combining the reactants or in the presence of an inert organic solvent such as tetrahydrofuran, dioxan, ethyl acetate, chloroform, dichloromethane, methanol, ethanol or pyridine.

3rd Step

The cyclization to obtain the diazepinone of general formula VIII is carried out using methods known per se, e.g. in an inert solvent in the presence of an acid catalyst such as acetic acid or silica gel with azeotropic removal of the water formed during cyclization.

4th Step

Conversion into the thione IX is carried out using phosphorus pentasulphide using conventional methods.

5th Step

This reaction step comprises the synthesis of the fused triazolo- or imidazolo group.

For this purpose, a compound of general formula IX may be reacted with an acid halide or with hydrazine and subsequently with an acid halide (preferably an acid chloride), or with an orthoester ($R_1$—C(OCH$_3$)$_3$).

The reaction of the thione with an acid halide is carried out in an inert organic solvent such as dioxan, dimethylformamide, tetrahydrofuran or a suitable hydrocarbon such as benzene or toluene at temperatures between ambient temperature and the boiling point of the reaction mixture. The end products are isolated by known methods, e.g. by crystallization.

The reaction of the thione IX with hydrazine is carried out in inert organic solvents such as tetrahydrofuran, dioxan, halogenated hydrocarbons such as methylene chloride or in suitable hydrocarbons, at temperatures between ambient temperature and the boiling point of the reaction mixture.

Further reaction with an acid halide IX or an orthoester is carried out in an inert organic solvent such as halogenated hydrocarbons, cyclic or open-chained aliphatic ethers, but may also be carried out directly in the substance. The end product IA is isolated by known methods, e.g. crystallization.

A process for preparing the imidazo-fused hetrazepines (X=CH) consists in reacting the thione IX with an α-aminoaldehyde-alkylacetal or with an α-aminoketone-alkylketal of general formula

wherein $R_1$ represents hydrogen or a $C_{1-4}$-alkyl group or a cyclopropyl group.

Analogous methods for synthesizing an acetal or ketal and an analogous method for cyclization are described in Swiss Patent No. 580 099.

6th Step

The protecting group is cleaved by hydrolysis using methods known per se, e.g. by heating in the presence of potassium hydroxide, sodium hydroxide, sodium methanolate, sodium methoxide, potassium ethanolate or sodium ethanolate, sodium methanolate or sodium ethanolate.

Method of synthesis B:

Compounds of general formula I wherein A represents one of the groups

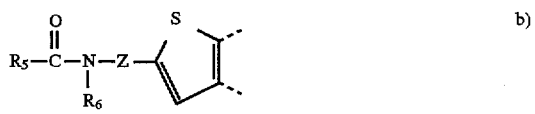

or

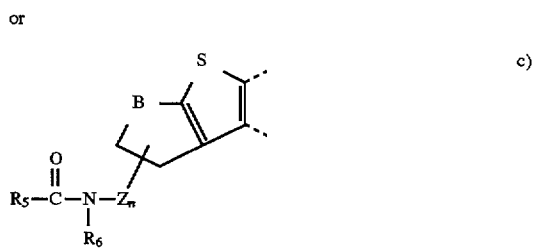

may be obtained by analogous methods by reacting the suitable amines of formula I wherein A represents

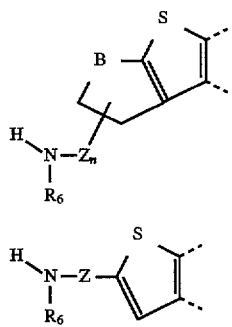

with reactive acid derivatives, particularly acid halides of formula $R_5$CO—halogen. The reaction may be carried out in inert organic solvents at elevated temperature.

The amines mentioned above may be synthesized, for example, analogously to those described in European Patent Applications 230 942 and 254 245.

EXAMPLE 1

3-(4-Chlorobenzoyl)-6-(2-chlorophenyl)-8,11-dimethyl-2,3,4,5-tetrahydro-4H-pyrido[4,3 :4',5'] thieno-[3,2-f][1,2,4]triazolo[4,3-a]-1,4-diazepine a) 4-Chlorobenzoylpiperidone 40.0 g (0.26 mol) of 4-piperidone hydrochloride (× H$_2$O) and 38.6 g of potassium carbonate are suspended in 300 ml of tetrahydrofuran. 45.4 g of 4-chlorobenzoyl chloride are added thereto with stirring and the mixture is reacted for 2 hours at ambient temperature and refluxed for 2 hours. The reaction mixture is evaporated down in vacuo, the residue is neutralized with 2N hydrochloric acid and extracted with dichloromethane. 38 g of a viscous oil are obtained from the organic phase after removal of the extraction agent.

$^1$H-NMR (CDCl$_3$): δ=7.40 (4H, s, aryl-H); 3.84 (4H, m, N—(CH$_2$)$_2$; 2.50 (4H, m, (CH$_2$)$_2$C=O).

b) 2-Amino-3-(2-chlorobenzoyl)-6-(4-chlorobenzoyl)-tetrahydropyrido[2,3-c]-thiopine A mixture of 16 g (70 mmol) of benzoylpiperidone, 12.7 g of o-chlorocyanoacetophenone and 2.3 g of sulphur in 50 ml of dimethylformamide is combined with 5 ml of triethylamine and stirred for 2 hours at 60°–70° C. The reaction mixture is evaporated down in vacuo and the residue is taken up in 100 ml of ethyl acetate. It is then washed with water, the organic phase is separated off, dried and evaporated down. The residue is crystallized from a mixture of ethyl acetate and ether. 17 to 18 g of the title compound are obtained in the form of yellow crystals, m.p. 208°–210° C.

$^1$H-NMR (CDCl$_3$): δ=7.68–7.19 (10 H, m, aryl-H, NH$_2$); 4.45 (2H, m, N—CH$_2$); 3.51 (2H, m, N—CH$_2$CH$_2$—); 1.81 (2H, m, N—CH$_2$CH$_2$—).

c) 2-(2-Bromopropionylamino)-3-(2-chlorobenzoyl)-6-(4-chlorobenzoyl)-tetrahydropyrido[2,3-c]-thiophene 17.0 g (39 mmol) of aminoketone are dissolved in 170 ml of dichloromethane, then 4.1 ml of pyridine are added, followed by the dropwise addition of 9.3 g of 2-bromopropionic acid chloride, with stirring, whilst the temperature is maintained at 20°–25° C. It is stirred for 1 hour at ambient temperature, the reaction mixture is evaporated down in vacuo and the residue is chromatographed on SiO$_2$ (dichloromethane/methanol 99:1). After elimination of the eluant 18 g of the title compound are obtained from the eluate in the form of crystals, m.p. 180°–182° C.

$^1$H-NMR (CDCl$_3$): δ=12.80 (1H, s, NH—C=O); 7.57–7.19 (8H, m, aryl-H); 4.62 (2H, m, N—CH$_2$); 4.67 (1H, qu, J=7Hz, CH—CH$_3$); 356 (2H, m, N—CH$_2$CH$_2$), 1.99 (3H, d, J=7Hz, CH—CH$_3$); 1.94 (2H, m, N—CH$_2$CH$_2$—).

d) 2-(2-Aminopropionylamino)-3-(2-chlorobenzoyl)-6-(4-chlorobenzoyl)-tetrahydropyrido[2,3-c]thiophene 18.0 g of aminopropionylketone are heated to 100° C. in an autoclave with 20 ml of ethyl acetate, 15 ml of dichloroethane and 2 g of liquid ammonia for 1 hour at 12–13 bar. The residue is evaporated down, taken up in dichloromethane and washed with water and the organic phase is dried after phase separation. After the solvent has been distilled off, 16 g of the title compound remain in the form of an amorphous residue which can be further used directly.

e) 3-(4-Chlorobenzoyl)-6-(2-chlorophenyl)-8-methyl-2,3,4,5-tetrahydro-4H-pyrido[4,3:4', 5']thieno-[3,2-f][1,4]diazepin-9-one 16 g of crude aminopropionylaminoketone are mixed with 250 ml of toluene and 100 g of silica gel and refluxed for 2 hours using a water separator. After cooling the mixture is suction filtered and the residue is extracted three times with 200 ml of boiling methanol. The methanol extracts are combined and evaporated down and the residue is chromatographed on SiO$_2$ (dichloromethane). After evaporation, crystallization from an ethyl acetate/ether mixture yields 6 g of title compound in the form of crystals, m.p. 258°–260° C.

f) 3-(4-Chlorobenzoyl)-6-(2-chlorophenyl)-8-methyl-2,3,4,5-tetrahydro-4H-pyrido [4,3:4',5']thieno-[3,2-f][1,4]diazepin-9-thione (10 mmol) of the diazepine prepared by the above process, 50 ml of diethyleneglycol-dimethylether (diglyme) and 1.7 g of sodium hydrogen carbonate are mixed with 2.5 g of phosphorus pentasulphide with stirring and stirred for 1.5 hours at 65°–70° C. The reaction mixture is poured onto ice water and suction filtered and the crystals are taken up in a dichloromethane/methanol mixture. After repeated filtration the mixture is evaporated down, the remaining water is azeotropically distilled off with toluene and the residue is chromatographed over SiO$_2$ (methanol/dichloromethane). 3.1 g of the title compound are obtained from the eluate in the form of yellow crystals which melt at 238° C.

3 g of this thione are dissolved in 30 ml of tetrahydrofuran and combined with 0.32 g of hydrazine hydrate. The mixture is stirred for a further 30 minutes at ambient temperature, evaporated down in vacuo and the residue is mixed with ether, whereupon crystallization sets in. 2.2 g of crystals are obtained, m.p. 170°–175° C. These are refluxed for 1 hour in 20 ml of alcohol and 1.2 ml of ethyl orthoacetate. The reaction mixture is evaporated down in vacuo and the residue is chromatographed. 2.2 g of the title compound are obtained in the form of colorless crystals, m.p. 269°–271° C.

The same compound is obtained if 4.5 g of 3-(4-chlorobenzoyl)-6-(2-chlorophenyl)-8-methyl-2,3,4,5-tetrahydro-4H-pyrido[4,3:4',5']thieno[3,2-f]-1,4-diazepin-9-one are stirred with 80 ml of absolute dioxane and 10.5 g of phosphorus pentachloride for 1 hour at ambient temperature, then 15 g of acetic acid hydrazide are added to the reaction mixture (imide chloride) and stirring is continued for 30 minutes. The mixture is carefully evaporated down, the residue is combined with water, the product is extracted with dichloromethane and, from the combined eluates, the open-chained compound is obtained in the form of dark red crystals which are cyclised by heating with 10 g of SiO$_2$ in 50 ml of toluene to obtain the title compound.

$^1$H-NMR (DMSO-d6): δ=7.65–7.19 (8H, m, aryl-H); 5.03, 4.67 (2H, m, N—CH$_2$); 4.34 (1H, qu, J=7 Hz, CH—CH$_3$); 4.05, 3.36 (2H, m, N—CH$_2$CH$_2$—); 2.59 (3H, s, triazole-CH$_3$); 2.19, 1.50 (2H, m, N—CH$_2$CH$_2$); 1.88 (3H, d, J=7Hz, —CH—CH$_3$).

Separation of enantiomers using a chiral column 2 g of the racemate are dissolved in 25 ml of a mixture of cyclohexane and dioxan 1:1 (ultrasound bath). This solution is added to a Chirasphor column made by E. Merck of Darmstadt (particle size 5 μm) and eluted in a recycling operation with cyclohexane/dioxan. After total separation of the enantiomers the solutions are worked up preparatively. The first eluate obtained is isomer (1a) with $[α]_D^{20}$+36.8 (methanol) and the second eluate yields the isomer (1b) with $[α]_D^{20}$–36.8° (methanol).

EXAMPLE 2

3-(4-Isobutylbenzoyl)-6-(2-chlorophenyl)-8,11-dimethyl-2,3,4,5-tetrahydro-4H-pyrido[4,3:4',5'] thieno-[3,2-f][1,2,4]triazolo[4,3-a]1,4diazepine a) Starting from N-acetylpyridone, first the 3-acetyl-6-(2-chlorophenyl)-8-methyl-2,3,4,5-tetrahydro-4H-pyrido[4,3:4,5][3,2-f]-1,4-diazepin-9-one is synthesized analogously to Example 1. From this, the 3-thioacetyl-6-(2-chlorophenyl)-8,11-dimethyl-2,3,4,5-tetrahydro-4H-pyrido[4,3:4',5']thieno-[3,2-f]-1,2,4-triazolo[4,3-a]-1,4-diazepine is obtained in the form of crystals m.p. 290°–291° C.

$^1$H-NMR (CDCl$_3$): δ=7.53–7.10 (8H, m, aryl-H); 5.06, 4.67 (2H, m, N—CH$_2$—); 4.30 (1H, qu, J=7Hz, CH—CH$_3$); 3.64, 339 (2H, m, N—CH$_2$CH$_2$—); 2.68 (3H, s, CH$_3$-triazole); 2.50 (2H, d, J=6Hz, CH$_2$—CH); 2.21, 1.87 (2H, m, N—CH$_2$CH$_2$—); 2.12 (3H, d, J=7Hz, CH—CH$_3$); 1.89 (1H, m, CH(CH$_3$)$_2$); 0.90 (6H, d, J=7Hz, CH(CH$_3$)$_2$).

Analogously to the process described earlier in our European Patent Application 204 245, the nor-compound 6-(2- chlorophenyl)-8,11-dimethyl-2,3,4,5-tetrahydro-4H-pyrido[4,3:4',5']thieno[3,2-f]-1,2,4-triazolo[4,3-a]-1,4-diazepine is obtained therefrom by saponification with methanolic potassium hydroxide solution in the form of crystals m.p. 205°–207° C.

15 g (39 mmol) of this nor-compound are dissolved or suspended in 250 ml and mixed with 5.9 dichloromethane/triethylamine. With stirring and cooling with ice, 7.7 g of 4-isobutylbenzoylchloride are added dropwise at 10°–15° C. and the mixture is stirred for 30 minutes. It is washed with water, the organic phase is separated off, partially evaporated down and the residue is chromatographed on $SiO_2$ (dichloromethane/methanol 97:3). After crystallization from a mixture of dichloromethane/ether, 12.5 g of the title compound are obtained in the form of crystals, m.p. 248°–250° C. The 4-isobutyl-benzoylchloride can be synthesized as shown on page 34.

$^1$H-NMR ($CDCl_3$): δ=7.56–7.20 (4H, m, aryl-H); 5.07, 4.47 (2H, m, N—$CH_2$); 4.30 (1H, qu, J=7Hz, CH—$CH_3$); 3.75, 3.40 (2H, m, N—$CH_2CH_2$); 2.74 (1H, m, CH—C=O); 2.69 (3H, s, $CH_3$-triazole); 2.19, 1.74 (2H, m, N—$CH_2CH_2$); 2.13 (3H, d, J=8Hz, CH—$CH_3$); 1.11 (6H, d, —$CH(CH_3)_2$).

b) 4-Isobutylbenzaldehyde 134 g of isobutylbenzene are mixed in an autoclave with 206 g of benzene and 145.5 g of aluminum chloride and saturated with dry HCl gas (2–3 bar). Then carbon monoxide is forced in until a pressure 35–40 bar is reached and the mixture is stirred for 4 hours at 25° C. The reaction mixture is poured onto 1 kg of ice, the organic phase is separated off, washed with dilute hydrochloric acid, water and sodium hydrogen carbonate solution and then evaporated down. The residue is distilled. From the main fraction ($Bp_{15}$: 122°–125° C.) 100 g of the title compound are obtained corresponding to 61.6% of theory.

$^1$H-NMR ($CDCl_3$): δ=9.99 (1H, s, CH=O); 7.77, 7.28 (4H, 2d, J=9Hz, aryl-H); 2.55 (2H, d, J=6Hz, $CH_2$—CH); 1.90 (1H, m, $CH_2$—CH—); 0.92 (6H, d, J=7Hz, $CH(CH_3)_2$).

c) 4-Isobutylbenzoic acid 39 g of the aldehyde prepared by the process described above are mixed with 560 ml of 2N sodium hydroxide solution. Gradually, 24 g of potassium permanganate are added with vigorous stirring. The mixture is stirred for a further 12 hours at ambient temperature, suction filtered over kieselguhr and then the filtrate is acidified with conc. hydrochloric acid. The crystals obtained are suction filtered and dried. A yield of 16–17 g of the title compound is obtained in the form of crystals, m.p. 138°–140° C.

d) 4-Isobutylbenzoylchloride 16.2 g of the carboxylic acid prepared by the process described above are refluxed for 4 hours with 50 ml of benzene and 7.5 ml of pure thionyl chloride. After removal of the solvent the residue is distilled in vacuo ($Bp_{18}$: 139°–141° C.). The title compound is obtained in a yield of 12 to 13 g.

EXAMPLE 3

6-(2-Chlorophenyl)-4H-1-methyl-8-[N-(4-chlorophenyl-carbonyl)-N-methyl-3-aminopropyl]-thieno [3.2-f]-[1.2.4]triazolo[4.3-a][1.4]diazepine 6-(2-Chlorophenyl)-4H-8-[2-(methoxycarbonyl)-ethyl]-1-methylthieno[3.2-f][1.2.4]triazolo[4.3-a][1.4]diazepine is refluxed for 4 to 6 hours in all in a system comprising $NaBH_4$/tert.-butanol/methanol, the completion of reduction is monitored by thin layer chromatography (silica gel, eluant methylene chloride/methanol (9:1), the resulting alcohol is recrystallized from acetone and then converted into the corresponding mesylate in dichloromethane using methanesulphonic acid chloride/triethylamine. The mesylate is reacted with methylamine within a reaction time of 3 hours at 120° C. under a pressure of 11.4 bar and the resulting N-methyl-3-aminopropyl derivative is converted into the desired amide in pyridine/dioxan using 4-chlorobenzoyl chloride in a 50% yield, the amide being obtained as a bright yellow amorphous powder.

$^1$H-NMR ($CDCl_3$);δ=7.52–7.19 (8H, m, aryl-H); 6.43 (1H, s, thiophene-H); 4.92 (2H , s, $CH_2$-7 ring); 3.86 (2H, m, N—$CH_2$); 2.86 (3H, s, N—$CH_3$); 2.84 (2H, m, N—$CH_2$—$CH_2$—$CH_2$—); 2.69 (3H, s, $CH_3$-triazole); 1.99 (2H, m, N—$CH_2$—$CH_2$—$CH_2$—).

EXAMPLE 4

6-(2-Chlorophenyl)-4H-1-methyl-8-[N-(4-chlorophenyl-carbonyl)-N-ethyl-aminomethyl]-thieno[3.2-f][1.2.4]-triazolo[4.3-e][1.4]diazepine Starting from 6-(2-chlorophenyl)-8-formyl-4H-1-methyl-thieno[3.2-f][1.2.4]triazolo[4.3-a][1.4]diazepine and ethylamine, the intermediate compound 6-(2-chlorophenyl)-4H-1-methyl-8-(N-ethyl)-aminomethyl-thieno[3.2-f][1.2.4]triazolo [4.3-a][1.4]diazepine is obtained by reductive amination in methanol as the solvent and Raney nickel as catalyst with quantitative hydrogen uptake at ambient temperature within a reaction time of 3 hours, the compound being in the form of crystals m.p. 153°–155° (diisopropylether) in a 43% yield.

The intermediate compound is subsequently reacted with 4-chloro-benzoylchloride in a pyridine/dioxan mixture and the reaction mixture is purified by flash chromatography on silica gel using dichloro-methane/methanol (9:1) as eluant. The title compound is obtained as a bright yellow amorphous powder in a 65% yield.

$^1$H-NMR ($CDCl_3$):δ=7.50–7.22 (8H, m, aryl-H); 6.61 (1H, s, thiophene-H); 4.95 (2 H, s, $CH_2$.7-ring); 4.68 (2H, s, N—$CH_2$); 3.30 (2H, m, N—$CH_2$—$CH_3$); 2.74 (3H, s, $CH_3$-triazole); 1.15 (3H, t, J=7Hz, N—$CH_2$—$CH_3$)

Analogously to the general method of synthesis described and analogously to Examples 1 and 2 the following compounds of general formula Ia

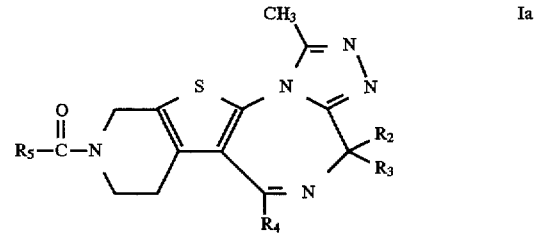

may be synthesized wherein $R_4$ represents ortho-chlorophenyl and $R_2$, $R_3$ and $R_5$ are as defined in the Table.

| No. | R₅ | R₂ | R₃ | M.p. °C. |
|---|---|---|---|---|
| 1 | 2-thienyl | H | H | |
| 2 | 2-thienyl | H | CH₃ | NMR 256–257 |
| 3 | 2-furyl | H | CH₃ | NMR 253–255 |
| 4 | 2-furyl | H | H | |
| 5 | 1-naphthyl | H | CH₃ | |
| 6 | 1-naphthyl | H | H | |
| 7 | 4-cyanophenyl | H | CH₃ | 260–262 |
| 8 | 4-cyanophenyl | H | H | |
| 9 | 4-iodophenyl | H | CH₃ | |
| 10 | 2-iodophenyl | H | H | |
| 11 | CCl₃ | H | CH₃ | |
| 12 | (CH₃)₃C-CH₂- | H | CH₃ | |

-continued

| No. | R₅ | R₂ | R₃ | M.p. °C. |
|---|---|---|---|---|
| 13 | (CH₃)₂CHCH₂— | H | H | |
| 14 | Cl—CH₂— | H | CH₃ | |
| 15 | —CH₂CH(Cl)CH₂Cl | H | H | |
| 16 | ClCH₂C(CH₃)₂— | H | CH₃ | |
| 17 | CH₃CHFCF₂CF₂CF₃ (perfluorinated fragment) | H | H | |
| 18 | 4-(pentyl)phenyl— | H | CH₃ | |
| 19 | 4-(hexyl)phenyl— | H | H | |
| 20 | 4-methylphenyl— | H | CH₃ | 258–259° C. |
| 21 | 4-ethylphenyl— | H | H | |
| 22 | 4-(2-propyl)phenyl— | H | CH₃ | |
| 23 | 4-butylphenyl— | H | CH₃ | 245–247 |
| 24 | 4-(trifluoromethyl)phenyl— | H | H | |
| 25 | 4-tert-butylphenyl— | H | CH₃ | 188–190° C. |
| 26 | 4-tert-butylphenyl— | H | H | |

-continued

| No. | R₅ | R₂ | R₃ | M.p. °C. |
|---|---|---|---|---|
| 27 | 4-(OCH₂CH₃)-C₆H₄- (4-ethoxyphenyl) | H | CH₃ | |
| 28 | 4-Cl-C₆H₄- | H | H | |
| 29 | 4-(OCH₃)-C₆H₄- | H | CH₃ | 210–212° C. |
| 30 | 4-F-C₆H₄- | H | H | |
| 31 | 3-(CF₃)-C₆H₄- | H | CH₃ | |
| 32 | 4-Br-C₆H₄- | H | H | |
| 33 | 3-CH₃-C₆H₄- | H | CH₃ | |
| 34 | 3,4-Cl₂-C₆H₃- | H | CH₃ | |
| 35 | 3-F-C₆H₄- | H | H | |
| 36 | 3-Cl-C₆H₄- | H | CH₃ | |
| 37 | 2,6-Cl₂-C₆H₃- | H | H | |
| 38 | 2,3,4,5,6-F₅-C₆- (pentafluorophenyl) | H | CH₃ | 225–227 |

-continued

| No. | R₅ | R₂ | R₃ | M.p. °C. |
|---|---|---|---|---|
| 39 | pentafluorophenyl | H | H | |
| 40 | 3,5-bis(trifluoromethyl)phenyl | H | CH₃ | |
| 41 | 3,5-bis(trifluoromethyl)phenyl | H | H | |
| 42 | 2,3,6-trifluorophenyl | H | CH₃ | |
| 43 | 2,4,5-trifluorophenyl | H | H | |
| 44 | pyridin-2-yl | H | CH₃ | |
| 45 | 2,2-dimethylbutyl (neopentyl-like) | H | CH₃ | |
| 46 | 2-chloro-6-methylpyridin-4-yl | H | H | |
| 47 | 2-chloro-6-methylpyridin-4-yl | H | CH₃ | |
| 48 | 2,6-dichloropyridin-4-yl | H | H | |

-continued

| No. | R₅ | R₂ | R₃ | M.p. °C. |
|---|---|---|---|---|
| 49 | 2-(propylthio)-3-methylpyridine group | H | CH₃ | |
| 50 | 1-phenyl-3,5-dimethyl-1,2,4-triazole group | H | H | |
| 51 | 3,5-dimethyl-4-isoxazolyl group | H | CH₃ | |
| 52 | 6-chloro-3-pyridyl group | H | H | |
| 53 | 2-(methylthio)-3-pyridyl group | H | CH₃ | |
| 54 | 3-methyl-5-phenyl-isoxazol-4-yl group (with O—N) | H | H | |
| 55 | benzothiophen-2-yl group | H | CH₃ | |
| 56 | 2,2-dimethylpentyl group | H | CH₃ | |
| 57 | 2,2-dimethylpentyl group | H | H | |
| 58 | 2,5-dimethylphenyl group | H | CH₃ | |
| 59 | 2,4-dimethylphenyl group | H | H | |
| 60 | 4-isopropoxyphenyl group | H | CH₃ | |

-continued

| No. | R₅ | R₂ | R₃ | M.p. °C. |
|---|---|---|---|---|
| 61 | 2-chloro-thiophene-5-yl | H | H | |
| 62 | 2,5-dichloro-3-methyl-thiophene-4-yl | H | CH₃ | |
| 63 | 2,5-dichloro-3-methyl-thiophene-4-yl | H | H | |
| 64 | 2,3-dichlorophenyl | H | CH₃ | |
| 65 | 2,5-dichlorophenyl | H | H | |
| 66 | 1,3-dichloro-2-methyl-2-(chloromethyl)propyl | H | CH₃ | |
| 67 | 4-(trifluoromethyl)phenyl | H | CH₃ | 305–307° C. |
| 68 | 4-(trifluoromethyl)phenyl | H | H | |
| 69 | 4-(trifluoromethyl)phenyl | CH₃ | CH₃ | |
| 70 | phenyl | H | H | |
| 71 | phenyl | H | CH₃ | 248–250° C. |
| 72 | phenyl | CH₃ | CH₃ | |
| 73 | (CH₃)₃C— | H | CH₃ | 255–257° C. |
| 74 | " | H | H | |
| 75 | " | CH₃ | CH₃ | |
| 76 | (CH₃)₂CH— | CH₃ | CH₃ | |
| 77 | " | H | CH₃ | 225–226° C. |
| 78 | 4-methylphenyl | CH₃ | CH₃ | |

-continued

| No. | R₅ | R₂ | R₃ | M.p. °C. |
|---|---|---|---|---|
| 79 | 4-CH₃-C₆H₄- | H | H | |
| 80 | 4-(CH₃)₃C-C₆H₄- | CH₃ | CH₃ | |
| 81 | 4-C₂H₅-C₆H₄- | H | H | |
| 82 | 4-C₂H₅-C₆H₄- | H | CH₃ | 255–256° C. |
| 83 | 4-C₂H₅-C₆H₄- | CH₃ | CH₃ | |
| 84 | 4-CH₃O-C₆H₄- | CH₃ | CH₃ | |
| 85 | 4-CH₃O-C₆H₄- | H | H | |
| 86 | 4-Cl-C₆H₄- | H | CH₃ | NMR |
| 87 | 4-Cl-C₆H₄- | H | H | 178–180 |
| 88 | 4-Cl-C₆H₄- | CH₃ | CH₃ | 242–247 |
| 89 | 4-N≡C-C₆H₄- | H | CH₃ | NMR 260–262 |
| 90 | 4-N≡C-C₆H₄- | H | H | |
| 91 | 4-N≡C-C₆H₄- | CH₃ | CH₃ | |
| 92 | 4-(CH₃)₂CH-CH₂-C₆H₄- | H | H | 242—243 |

-continued

| No. | R₅ | R₂ | R₃ | M.p. °C. |
|---|---|---|---|---|
| 93 | (CH₃)₂CH—CH₂—C₆H₄— | H | CH₃ | NMR 245–247 |
| 94 | (CH₃)₂CH—CH₂—C₆H₄— | CH₃ | CH₃ | |
| 95 | 4-pyridyl | CH₃ | CH₃ | |
| 96 | 2-furyl | CH₃ | CH₃ | |
| 97 | 4-(F₃C)—C₆H₄— | H | CH₃ | NMR 305–307 |
| 98 | 4-(F₃C)—C₆H₄— | CH₃ | CH₃ | |
| 99 | pentafluorophenyl | CH₃ | CH₃ | |
| 100 | 2,4-dimethoxyphenyl | H | CH₃ | |
| 101 | 2,5-dimethoxyphenyl | H | H | |
| 102 | 4-pyridyl | H | CH₃ | NMR 268 |
| 103 | 4-pyridyl | H | H | |
| 104 | 3-pyridyl | H | CH₃ | |
| 105 | 3-pyridyl | H | H | |

-continued

| No. | R₅ | R₂ | R₃ | M.p. °C. |
|---|---|---|---|---|
| 106 | 3-cyanophenyl | H | CH₃ | |
| 107 | quinoxalin-2-ylmethyl | H | H | |
| 108 | 2,4-dichlorophenyl | H | CH₃ | |
| 109 | 3,4-difluorophenyl | H | H | |
| 110 | CH₂CH₂CH₂I (propyl-I) | H | CH₃ | |

In Table I the symbol "." indicates that a substituent is repeated.

The following are the 1H-NMR spectra of selected compounds of Table I above.

EXAMPLE 2

$^1$H-NMR (DMSO-d6): δ=7.81–7.09 (7H, m, aryl- and thiophene-H); 5.06, 4.81 (2H, m, N—CH₂); 4.34 (1H, qu, J=7Hz, CH—CH₃); 3.34 (2H, m, N—CH₂CH₂); 2.59 (3H, s, CH₃-triazole); 2.27, 1.60 (2H, m, N—CH₂CH₂—); 1.89 (3H, d, J=7Hz, CH—CH₃).

EXAMPLE 3

$^1$H-NMR (DMSO-d6): δ=7.83; 7.02; 6.63 (3H, 3 m, furan-H); 7.59–7.30 (4H, m, aryl-H); 5.09; 4.77 (2H, m, N—CH₂); 4.26 (1H, qu, J=7Hz, CH—CH₃); 4.02; 336 (2H, m, N—CH₂—CH₂—); 2.59 (3H, s, CH₃-triazole); 2.27; 1.60 (2H, m, N—CH₂CH₂—); 1.88 (3H, d, J=7Hz, CH—CH₃)—

EXAMPLE 20

$^1$H-NMR (DMSO-d6): δ=7.53–7.12 (8H, m, aryl-H); 4.97, 4.65 (2H, m, N—CH₂); 4.34 (1H, qu, J=7Hz, CH—CH₃) 3.33 (2H, m, N—CH₂CH₂—); 2.58 (3H, s, CH₃-triazole); 2.33 (3H, s, CH₃-aryl); 2.19, 1.49 (2H, m, N—CH₂CH₂—); 1.88 (3H, d, J=7Hz, CH—CH₃).

EXAMPLE 25

$^1$H-NMR (DMSO-d6): δ=7.55–7.19 (8H, m, aryl-H); 4.96, 4.68 (2H, m, N—CH₂); 4.34 (1H, qu, J=7Hz, CH—CH₃); 3.33 (2H, m, N—CH₂CH₂); 2.58 (3H, s, CH₃-triazole); 2.20, 1.51 (2H, m, N—CH₂C₂—); 1.88 (3H, d, J=7Hz, CH—CH₃); 1.29 (9H, S, C—(CH₃)₃).

EXAMPLE 29

$^1$H-NMR (DMSO-d6): δ=7.57–6.91 (8H, m, aryl-H); 4.86, 4.68 (2H, m, N—CH₂); 4.33 (1H, qu, J=7Hz, CH—CH₃); 3.78 (3H, s, OCH₃); 3.32 (2H, m, N—CH₂CH₂—); 2.58 (3H, s, CH₃-triazole); 2.20, 1.51 (2H, m, N—CH₂CH₂); 1.88 (3H, d, J=7Hz, CH—CH₃).

EXAMPLE 57

$^1$H-NMR (DMSO-d6): δ=7.58–7.16 (8H, m, aryl-H); 4.96, 4.65 (2H, m, N—CH₂); 4.34 (1H, qu, J=7Hz, CH—CH₃); 3.32 (2H, m, N—CH₂—CH₃); 2.58 (3H, s, CH₃-triazole); 2.19, 1.51 (2H, m, N—CH₂CH₂—); 1.88 (3H, d, J=7Hz, CH—CH₃); 1.18 (3H, t, J=7.5 Hz, —CH₂—CH₃).

EXAMPLE 69

$^1$H-NMR (DMSO-d6): δ=8.60; 7.24 (4H, m, pyridine-H); 7.50–7.28 (4H, m, aryl-H); 4.84, 4.67 (2H, m, N—CH₂); 4.86 (1H, qu, J=7Hz, CH—CH₃); 3.61, 3.40, (2H, m, N—CH₂—CH₂—); 2.58 (2H, s, triazole-H); 2.21, 1.67 (2H, m, N—CH₂CH₂—); 1.93 (3H, d, J=7Hz, CH—CH₃).

EXAMPLE 73

$^1$H-NMR (CDCl₃): δ=7.53–7.19 (4H, m, aryl-H); 4.99; 4.55 (2H, m, N—CH₂—); 4.28 (1H, qu, J=7Hz, CH—CH₃); 3.86; 3.42 (2H, m, N—CH₂CH₂—); 2.68 (3H, s, CH₃-triazole); 2.13 (3H, d, J=7Hz, CH—CH₃); 2.15, 1.75 (2H, m, N—CH₂CH₂); 1.25 (9H, s, C(CH₃)₃).

EXAMPLE 82

$^1$H-NMR (DMSO-d6); δ=7.58–7.16 (8H, m, aryl-H); 4.96, 4.65 (2H, m, N—CH₂); 4.34 (1H, qu, J=7Hz, CH—CH₃); 3.32 (2H, m, N—CH₂CH₂—); 2.63 (2H, qu, J=7.5 Hz, —CH₂—CH₃); 2.58 (3H, s, CH₃-triazole); 2.19, 1.51 (2H, m, N—CH₂CH₂—); 1.88 (3H, d, J=7Hz, CH—CH₃); 1.18 (3H, t, J=7.5 Hz, —CH₂—CH₃).

EXAMPLE 86

$^1$H-NMR (CDCl₃): δ=7.57–7.19 (8H, m, aryl-H); 5.06, 4.65 (2H, m, N—CH₂); 4.28 (1H, qu, J=7Hz, CH—CH₃);

3.37 (2H, m, N—CH$_2$CH$_2$—); 2.68 (3H, s, CH$_3$ -triazole; 2.18, 1.73 (2H, m, N—CH$_2$—CH$_2$—); 2.12 (3H, d, J=7Hz, CH—CH$_3$).

EXAMPLE 89

$^1$H-NMR(DMSO-d6): δ=8.00–7.31 (8H, m, aryl-H); 5.02, 4.70 (2H, m, N—CH$_2$); 4.33 (1H, qu, J=7Hz, CH—CH$_3$); 3.32 (2H, m, N—CH$_2$CH$_2$); 2.61 (3H, s, CH$_3$-triazole), 2.20, 1.49 (2H, m, N—CH$_2$CH$_2$—); 1.88 (3H, d, J=7Hz, CH—CH$_3$).

EXAMPLE 92

$^1$H-NMR (CDCl$_3$): δ=7.53–7.10 (8H, m, aryl-H); 5.06, 4.67 (2H, m, N—CH$_2$—); 430 (1H, qu, J=7Hz, CH—CH$_3$); 3.64, 3.39 (2H, m, N—CH$_2$CH$_2$—); 2.68 (3H, s, CH$_3$-triazole); 2.50 (2H, d, J=6Hz, CH$_2$—CH); 2.21, 1.87 (2H, m, N—CH$_2$CH$_2$—); 2.12 (3H, d, J=7Hz, CH—CH$_3$); 1.89 (1H, m, CH(CH$_3$)$_2$); 0.90 (6H, d, J=7Hz, CH(CH$_3$)$_2$).

EXAMPLE 97

$^1$H-NMR (DMSO-d6): δ=7.89–7.28 (8H, m, aryl-H); 5.06, 4.70 (2H, m, N—CH$_2$); 4.34 (1H, qu, J=7Hz, CH—CH$_3$); 3.33 (2H, m, N—CH$_2$CH$_2$—); 2.62 (3H, s, CH$_3$-triazole); 2.20, 1.49 (2H, m, N—CH$_2$CH$_2$—); 1.88 (3H, d, J=7Hz, CH—CH$_3$).

Analogously to method of synthesis B described above and Examples 3 and 4 which are described in detail, compounds of the following structure, for example:

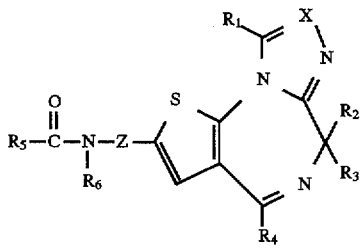

may be prepared, wherein R$_1$ represents methyl, R$_3$ represents hydrogen, R$_4$ represents ortho-chlorophenyl and R$_5$ represents 4-chlorophenyl and X, Z, R$_2$ and R$_6$ are as defined in the Table.

| Z | R$_2$ | R$_6$ | X |
|---|---|---|---|
| —CH$_2$— | —CH$_3$ | Et | N |
| —CH$_2$— | —CH$_3$ | Pr | N |
| —(CH$_2$)$_3$ | —CH$_3$ | Me | N |
| —(CH$_2$)$_3$— | —CH$_3$ | Me | H |
| —(CH$_2$)$_3$ | —H | Pr | CH |
| —(CH$_2$)$_7$ | —H | Me | N |
| —(CH$_2$)$_7$— | CH$_3$ | Me | N |
| —(CH$_2$)$_7$— | —CH$_3$ | Me | CH |

Et = Ethyl
Pr = n-Propyl
Me = Methyl

Galenic Preparations
Example a

| Tablets containing 10 mg of Substance B | |
|---|---|
| Composition | |
| Substance | 10 mg |
| Corn starch | 57 mg |
| Lactose | 48 mg |
| Polyvinylpyrrolidone | 4 mg |
| Magnesium stearate | 1 mg |
| | 120 mg |

Method of Preparation

The active substance, corn starch, lactose and polyvinylpyrrolidone are mixed together and moistened with water. The moist mixture is pressed through a 1.5 mm mesh screen and dried at about 45° C. The dry granules are passed through a 1.0 mm mesh screen and mixed with magnesium stearate. The finished mixture is compressed to form tablets in a tablet making press using dies 7 mm in diameter, provided with a dividing notch. Weight of tablet: 120 mg Substance B=3-(4-chlorobenzoyl)-6-(2-chlorophenyl)-8,11-dimethyl-2,3,4,5-tetrahydro-4H-pyrido [4,3:4',5'] thieno[3,2-f][1,2,4]-triazolo[4,3-a]-1,4-diazepine Example b

| Coated tablets containing 5 mg of Substance B | |
|---|---|
| Composition: | |
| Substance B | 5 mg |
| Corn starch | 41.5 mg |
| Lactose | 30 mg |
| Polyvinylpyrrolidone | 3 mg |
| Magnesium stearate | .5 mg |
| | 80 mg |

Method of Preparation

The active substance, corn starch, lactose and polyvinylpyrrolidone are thoroughly mixed and moistened with water. The moist mass is pressed through a 1 mm mesh screen, dried at about 45° C. and the granules are then passed through the same screen again. After the addition of magnesium stearate, convex tablet cores 6 mm in diameter are compressed in a tablet making machine. The tablet cores produced in this way are coated in known manner with a coating consisting essentially of sugar and talc. The finished coated tablets are polished with wax.

Weight of coated tablet: 130 mg

Example c

| Tablets containing 50 mg of Substance B | |
|---|---|
| Composition: | |
| Substance B | 50.0 mg |
| Calcium phosphate | 70.0 mg |
| Lactose | 40.0 mg |
| Corn starch | 35.0 mg |
| Polyvinylpyrrolidone | 3.5 mg |
| Magnesium stearate | 1.5 mg |
| | 200.0 mg |

Preparation:

Substance B, calcium phosphate, lactose and corn starch are uniformly moistened with an aqueous polyvinylpyrrolidone solution. The mass is passed through a 2 mm mesh screen, dried at 50° C. in a circulating air dryer and screened again. After the addition of the lubricant the granules are compressed in a tablet making machine.

Example d

Capsules containing 50 mg of Substance B

Composition:

| Substance B | 50.0 mg |
|---|---|
| Corn starch | 268.5 mg |
| Magnesium stearate | 1.5 mg |
| | 320.0 mg |

Preparation:

Substance B and corn starch are mixed together and moistened with water. The moist mass is screened and dried. The dry granules are screened and mixed with magnesium stearate. The finished mixture is packed into size 1 hard gelatine capsules.

Example e

Suppositories containing 50 mg of Substance B

Composition:

| Substance B | 50 mg |
|---|---|
| Solid fat | 1,650 mg |
| | 1,700 mg |

Preparation:

The hard fat is melted. At 40° C. the ground active substance is homogeneously dispersed therein. It is cooled to 38° C. and poured into slightly chilled suppository molds.

Example f

Oral suspension containing 50 mg of Substance B per 5 ml

Composition:

| Substance B | 50 mg |
|---|---|
| Hydroxyethylcellulose | 50 mg |
| Sorbic acid | 5 mg |
| 70% sorbitol | 600 mg |
| Glycerol | 200 mg |
| Flavoring | 15 mg |
| Water to | 5 ml |

Preparation:

Distilled water is heated to 70° C. Hydroxyethyl-cellulose is dissolved therein with stirring. After the addition of sorbitol solution and glycerol the mixture is cooled to ambient temperature. At ambient temperature the sorbic acid, flavoring and Substance B are added. In order to eliminate air from the suspension it is evacuated with stirring.

Obviously, the other PAF-antagonists according to the invention may be incorporated in the conventional galenic preparations in suitable doses.

An effective dose of the compounds according to the invention is between 1 and 100, preferably between 3 and 50 mg/dose, for oral administration, and between 0.001 and 50, preferably between 0.1 and 20 mg/dose for intravenous or intramuscular administration. Solutions containing 0.01 to 1.0, preferably 0.1 to 1% of active substance should be used for inhalation.

What is claimed is:

1. A hetrazepine of formula Ia,

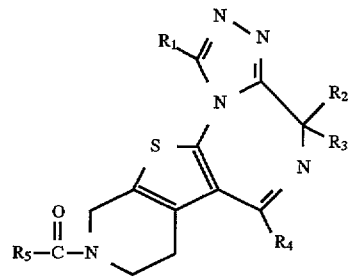

Ia wherein $R_1$ is hydrogen or methyl;

$R_2$ is hydrogen or methyl;

$R_3$ is hydrogen or methyl;

$R_4$ is phenyl optionally substituted in the 2-position by halogen;

$R_5$ is $C_{1-4}$-alkyl or $R_5$ is a group

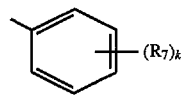

wherein $R_7$ is hydrogen, halogen, nitro, trifluoromethyl, branched or unbranched $C_{1-8}$-alkyl optionally substituted by halogen or hydroxy, $C_{3-6}$-cycloalkyl optionally substituted by halogen or hydroxy, branched or unbranched $C_{1-4}$-alkoxy, $C_{1-4}$-alkyl—S—, HS—, amino, $C_{1-6}$-alkylamino, or $C_{1-6}$-dialkylamino, k is 1, 2 or 3, whilst if k is greater than 1, $R_7$ may be identical or different; or $R_5$ is pentafluorophenyl, or a group:

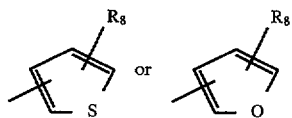

wherein $R_8$ is hydrogen, halogen or $C_{1-4}$-alkyl.

2. The hetrazepine as recited in claim 1 wherein $R_1$ is $CH_3$;

$R_2$ is hydrogen;

$R_3$ is hydrogen or methyl;

$R_4$ is ortho-chlorophenyl;

$R_5$ is a group

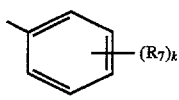

wherein $R_7$ is hydrogen, halogen, trifluoromethyl, branched or unbranched $C_{1-4}$-alkyl, branched or unbranched $C_{1-4}$-alkoxy, k is 1, 2 or 3, whilst if k is greater than 1, $R_7$ may be identical or different; or $R_5$ is pentafluorophenyl; or $R_5$ is a group:

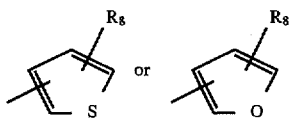

wherein $R_8$ is hydrogen.

3. The heterazepine as recited in claim 1 wherein $R_4$ is a phenyl ring substituted in the 2- position by chlorine and $R_5$ is a group

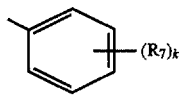

wherein

R7 is $C_{1-4}$-alkyl.

4. The heterazepine as recited in claim 1 wherein $R_1$ is $CH_3$;

$R_2$ is hydrogen;

$R_3$ is hydrogen or methyl;

$R_4$ is ortho-chlorophenyl;

$R_5$ is a group

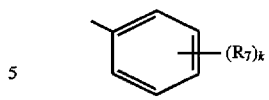

wherein $R_7$ is hydrogen, methyl, tert.-butyl, iso-butyl, sec.-butyl, methoxy, trifluormethyl, ethyl, or chloro.

5. The heterazepine as recited in claim 2, wherein $R_5$ is 2-thiophene or 2-furan.

6. 3-(4-Chlorobenzoyl)-6-(2-chlorophenyl)-8-11-dimethyl-2,3,4,5-tetrahydro-4H-pyrido-[4,3:4',5']thieno-[3,2-f][1,2,4]triazolo[4,3-a]-1,4-diazepine.

7. A pharmaceutical composition of matter comprising a therapeutically effective amount of a hetrazepine as recited in claim 1 and a pharmaceutically acceptable inert carrier.

8. A pharmaceutical composition of matter comprising a therapeutically effective amount of a hetrazepine as recited in claim 6 and a pharmaceutically acceptable inert carrier.

9. A method of treating disease in a warm-blooded animal induced by endogenously formed PAF which comprises administering to said animal a therapeutically effective amount of a hetrazepine as recited in claim 1.

10. A method of treating disease in a warm-blooded animal induced by endogenously formed PAF which comprises administering to said animal a therapeutically effective amount of a hetrazepine as recited in claim 6.

* * * * *